(12) United States Patent
Tour et al.

(10) Patent No.: US 11,478,489 B2
(45) Date of Patent: Oct. 25, 2022

(54) SELECTIVE ACCRETION OF CYTOPROTECTANT IN RADIATION-SENSITIVE TISSUES AND USES THEREOF

(71) Applicants: WILLIAM MARSH RICE UNIVERSITY, Houston, TX (US); THE BOARD OF TRUSTEES OF THE LELAND STANFORD JUNIOR UNIVERSITY, Stanford, CA (US); BOARD OF REGENTS, UNIVERSITY OF TEXAS SYSTEM, Austin, TX (US)

(72) Inventors: James Tour, Bellaire, TX (US); Cullen Taniguchi, Houston, TX (US); Kathy Mason, Houston, TX (US)

(73) Assignees: WILLIAM MARSH RICE UNIVERSITY, Houston, TX (US); THE BOARD OF TRUSTEES OF THE LELAND STANFORD JUNIOR UNIVERSITY, Stanford, CA (US); BOARD OF REGENTS, UNIVERSITY OF TEXAS SYSTEM, Austin, TX (US)

( * ) Notice: Subject to any disclaimer, the term of this patent is extended or adjusted under 35 U.S.C. 154(b) by 233 days.

(21) Appl. No.: 16/766,025

(22) PCT Filed: Nov. 19, 2018

(86) PCT No.: PCT/US2018/061888
§ 371 (c)(1),
(2) Date: May 21, 2020

(87) PCT Pub. No.: WO2019/103983
PCT Pub. Date: May 31, 2019

(65) Prior Publication Data
US 2020/0360406 A1 Nov. 19, 2020

Related U.S. Application Data

(60) Provisional application No. 62/589,155, filed on Nov. 21, 2017.

(51) Int. Cl.
*A61N 5/00* (2006.01)
*A61K 31/661* (2006.01)
(Continued)

(52) U.S. Cl.
CPC .............. *A61K 31/661* (2013.01); *A61N 5/10* (2013.01); *A61P 39/00* (2018.01); *A61N 2005/1094* (2013.01)

(58) Field of Classification Search
CPC ... A61N 5/10; A61N 2005/1094; A61P 39/00; A61K 31/661
See application file for complete search history.

(56) References Cited

U.S. PATENT DOCUMENTS

| 9,408,882 B2 | 8/2016 | Dadachova et al. |
| 2002/0035093 A1* | 3/2002 | Stogniew ................ A61P 1/02 514/625 |

(Continued)

FOREIGN PATENT DOCUMENTS

| CN | 102210694 A | 10/2011 |
| WO | 2007047315 A1 | 4/2007 |

OTHER PUBLICATIONS

Kemp G, Rose P, Lurain J, et al. Amifostine pretreatment for protection against cyclophosphamide-induced and cisplatin-induced toxicities: results of a randomized control trial in patients with advanced ovarian cancer. J Clin Oncol. 1996;14(7):2101-2112. doi:10.1200/JCO.1996.14.7.2101.

(Continued)

*Primary Examiner* — Samuel G Gilbert
(74) *Attorney, Agent, or Firm* — Guy Levi; The IP Law Firm of Guy Levi, LLC

(57) ABSTRACT

The disclosure relates to the treatment of primary and metastatic cancer using radiation. Specifically, the disclosure relates to methods providing for the selective accretion of cytoprotective agent in tissues and/or organs, sensitive to radiation that are adjacent to malignant tumors prior to radiation of the tumors at a dose that otherwise would be toxic to the tissues and/or organs, but are necessary to achieve ablative outcome on the tumors.

12 Claims, 6 Drawing Sheets

(51) Int. Cl.
*A61P 39/00* (2006.01)
*A61N 5/10* (2006.01)

(56) References Cited

U.S. PATENT DOCUMENTS

2003/0022867 A1* 1/2003 Stogniew .............. A61K 31/54
514/625
2013/0137916 A1 5/2013 Goer

OTHER PUBLICATIONS

Bonner HS, Shaw LM. New dosing regimens for amifostine: a pilot study to compare the relative bioavailability of oral and subcutaneous administralion with intravenous infusion. J Clin Pharmacol. 2002;42(2):166-174. doi:10.1177/00912700222011201.

* cited by examiner

SELECTIVE ACCRETION OF CYTOPROTECTANT IN RADIATION-SENSITIVE TISSUES AND USES THEREOF

CROSS REFERENCE TO RELATED APPLICATIONS

This patent application is a U.S. National Phase filing of commonly owned PCT Application No. PCT/US2018/061888, filed Nov. 19, 2018, claiming priority from U.S. Provisional Patent Application No. 62/589,155, filed Nov. 21, 2017, both which are incorporated herein by reference in their entirety.

BACKGROUND

The disclosure is directed to the treatment of primary and metastatic cancer using radiation. Specifically, the disclosure is directed to methods providing for the selective accretion of cytoprotective agent in tissues and/or organs that are sensitive to radiation and are also adjacent to malignant tumors prior to radiation of the tumors.

The major limiting factor in delivering the appropriate tumoricidal dose of radiation is toxicity to normal tissue in adjacent organs. This issue is highlighted by solid tumors of the abdomen and pelvis, such as pancreatic and prostate adenocarcinoma, which often cannot achieve tumoricidal doses without significant morbidity to the gastrointestinal (GI) tract. For example, pancreatic cancer often occurs in the head of the pancreas, which shares blood supply with the duodenum, which is a radiosensitive portion of the intestinal tract. Tumors of the pancreatic head require doses that exceed 77 Gy to achieve local control, which is often impossible to administer safely because the adjacent duodenum can only tolerate a maximum of 50 Gy without causing bleeding ulcers or perforation. Unfortunately for patients with unresectable pancreatic cancer, there are no effective treatments that specifically protect the GI tract from this radiotoxicity, and thus ablative radiotherapy in non-resectable pancreatic cancer is currently impossible.

WR-2721 (S-2-[3-aminopropylamino]-ethylphosphorothioic acid), also known as amifostine (and used herein interchangeably), is a proven radioprotector of normal tissues and is FDA-approved for intravenous (IV) administration. When given intravenously, amifostine causes severe nausea and hypotension, which is why it is administered to the patient after their drinking a large amount of liquids, and while lying down with blood pressure being continuously monitored. WR-2721 exists as a pro-drug that is hydrolyzed to the active cytoprotective free thiol metabolite, WR-1065 by non-specific tissue alkaline phosphatases that are enriched in normal (in other words, non-malignant) tissues. Unfortunately, these ubiquitous cellular enzymes present in the endothelium may mediate undesirable side effects in the autonomic nervous system.

WR-2721, which was formulated for oral delivery (see e.g., U.S. Pat. No. 5,167,947), was reformulated to increase plasma concentrations, because of significant enteral metabolism, which would preclude therapeutic levels from accumulating in the serum and reaching the target organs.

The disclosure addresses the shortcomings described above thereby demonstrating that oral WR-2721 is an effective radioprotector against otherwise lethal doses of radiation directed to radiation-sensitive tissues and/or organs wherein it can selectively accumulate its active metabolite, WR-1065, in significantly higher levels in the organ and/or tissue sought to be protected, over the nearby cancerous tissue.

SUMMARY

In an embodiment, provided is a method for treating a cancer patient with a combination therapy, comprising: administering to the patient a therapeutically effective, orally dosed cytoprotective pro-drug at a predetermined time prior to exposure to radiation, the patient having at least one of a primary and a metastatic cancer in at least one of a tissue and an organ adjacent to at least one of other tissues and other organs sensitive to radiation; and exposing the at least one tissue and one organ to a therapeutically effective radiation dose.

In another embodiment, provided herein is a method of protecting at least one of a first tissue and a first organ, the first tissue and/or organ being sensitive to radiation in a patient in need of a high dose radiation, from the high dose radiation to at least one of an adjacent second organ and an adjacent second tissue, comprising a step of administering to the patient an oral composition comprising a pharmaceutically effective concentration of a cytoprotective agent having a metabolite adapted to selectively accrete in at least the first tissue and the first organ, wherein the oral composition is administered at a predetermined time prior to radiation.

In yet another embodiment, provided herein is use of orally dosed cytoprotective pro-drug in the manufacture of a medicament for the treatment of a cancer patient having at least one of a primary and a metastatic cancer in at least one of a tissue and an organ adjacent to at least one of other tissues and other organs sensitive to radiation, wherein the medicament is configured to be orally administered at a predetermined time prior to exposing at least one of the other tissue and other organ, to radiation.

BRIEF DESCRIPTION OF THE DRAWINGS

The features of the methods for selectively accreting a radioprotectant in a radiation-sensitive healthy tissue and/or organ, prior to exposure of an adjacent tissue and/or organ to otherwise toxic radiation, will become apparent from the following detailed description when read in conjunction with the drawings, which are exemplary, not limiting, and wherein like elements are numbered alike in several figures and in which.

Figure 4:
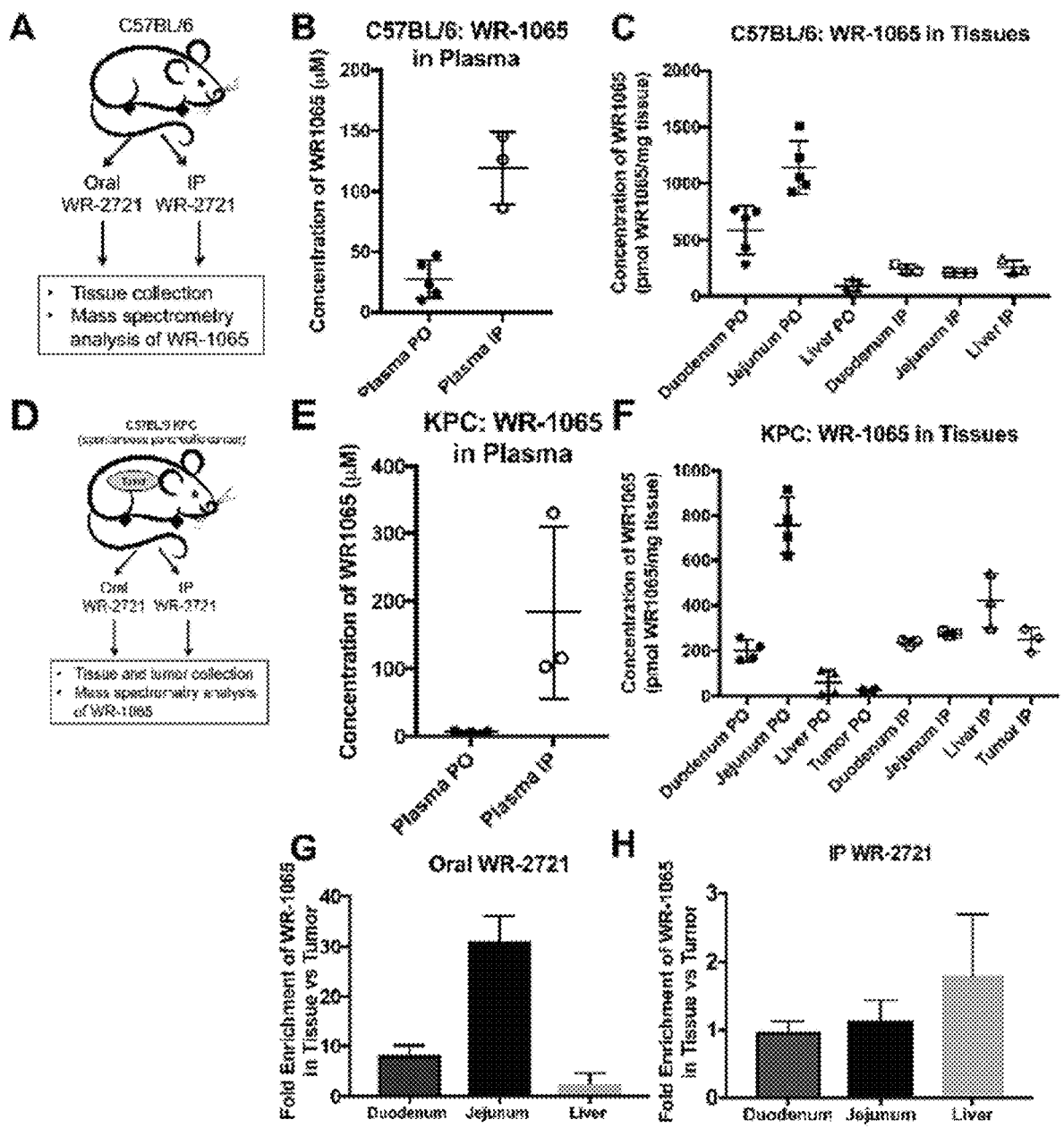
Figure 5:
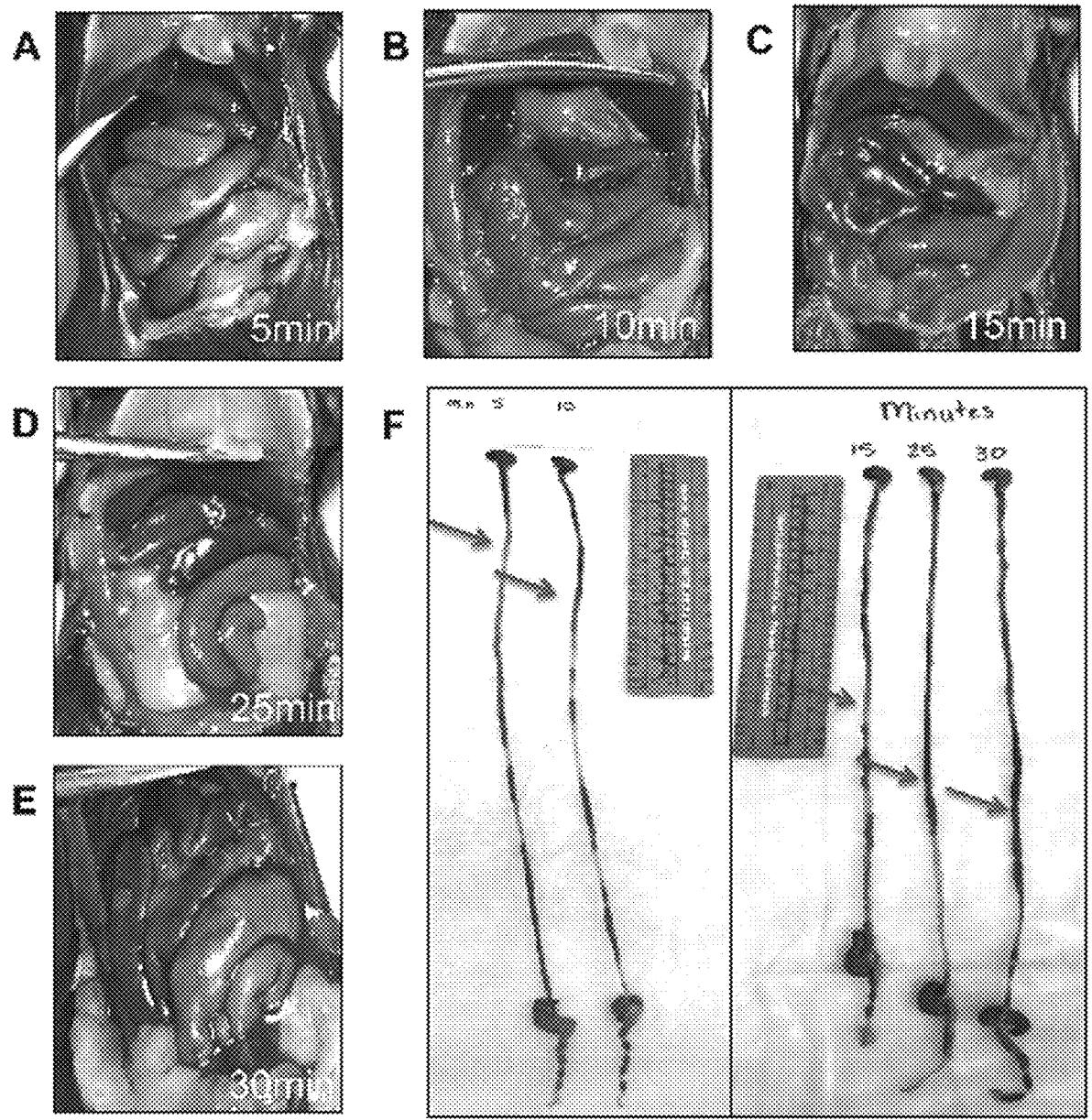
Figure 6:
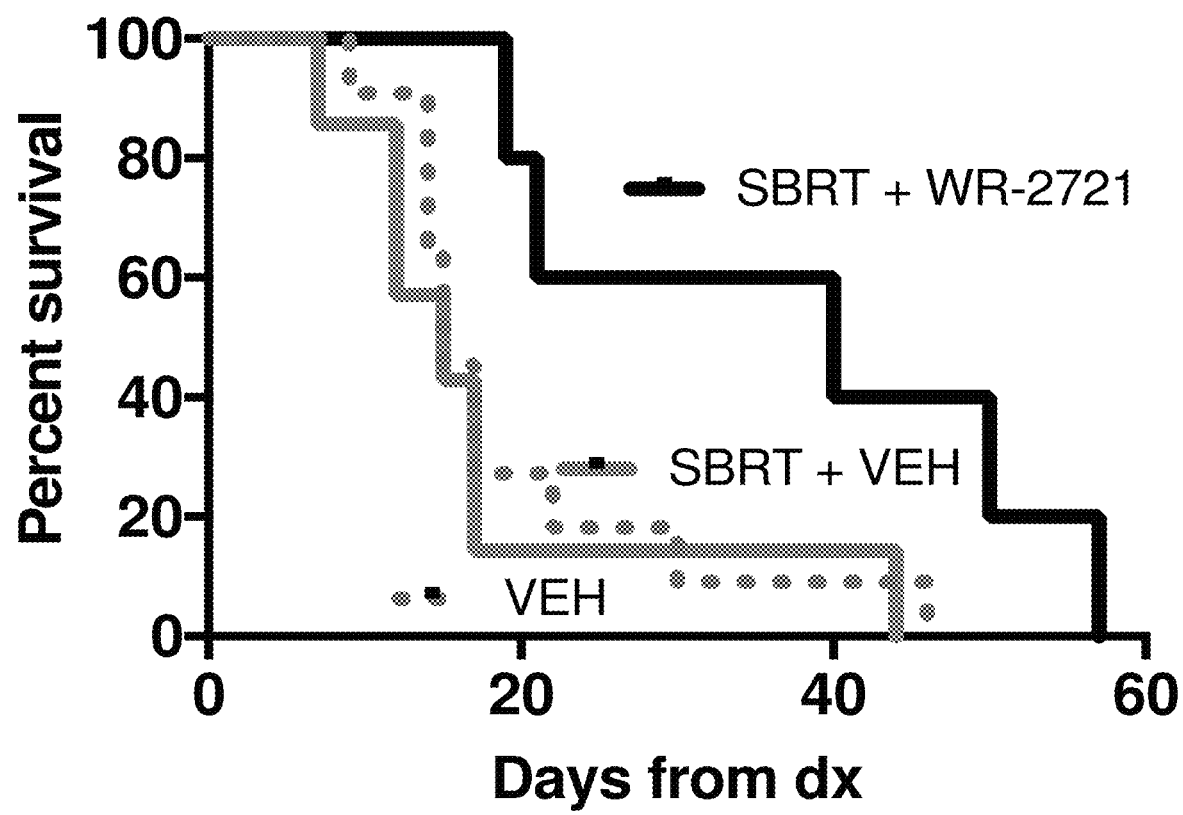

FIG. 4, shows selective enrichment (accretion) of the radioprotective metabolite WR-1065 by oral gavage (A) Schema of C57BL/6 mice treated with WR-2721 at 500 mg/kg PO or 250 mg/kg IP at 25 minutes prior to blood and tissue collection for LC/MS-MS analysis. C57BL/6 plasma concentrations (B) and C57BL/6 duodenum, jejunum and liver concentrations (C). Schema for WR-1065 determination in KPC animals shown in (D). (E) KPC plasma concentrations and (F) KPC duodenum, jejunum, liver and pancreatic tumor concentrations after oral and IP injections. (G-H) Data from (F) reformatted to show as ratio of WR-1065 in the noted tissue compared to spontaneous tumors;

FIG. 5 shows GI transit time following oral administration of methylene blue. (A-E) Show the location of methylene blue dye within the GI tract in situ following oral gavage at (A) 5 min (B) 10 min (C) 15 min (D) 25 min and (E) 30 min time points. (F) Comparison of resected GI tract from stomach to colon from the same mice shown in AE. Arrows indicate the dye front; and FIG. 6, shows survival following treatment using WR-2721 on KPC Mice treated to vehicle alone, SBRT with vehicle or SBRT with oral WR 2721. The SBRT field was 10 mm given AP/PA to the tumor and the dose was 12.5 Gy per day for 5 consecutive days for a total dose of 62.5 Gy (EQD2=117.2 Gy; $\alpha/\beta_{10}$=140.6). The tumors were identified by micro CT and ultrasound on a daily basis without fiducials. WR-2721 of vehicle was given 25 minutes prior to irradiation for each fraction.

While the disclosure is amenable to various modifications and alternative forms, specifics thereof have been shown by way of example in the figures and will be further described in detail hereinbelow.

It should be understood, however, that the intention is not to limit the disclosure to the particular embodiments described. On the contrary, the intention is to cover all modifications, equivalents, and alternatives.

DETAILED DESCRIPTION

The disclosure relates in one embodiment to methods of treating cancer using radiation, where the tumor location is adjacent to radiation sensitive tissue and the radiation dosage necessary for appropriate tumoricidal effect is toxic to the adjacent tissue and/or organs.

Pancreatic cancer requires a biologically equivalent dose of more than 77 Gy to have a clinical benefit. Currently, this is not attainable for most pancreatic tumors unless they are in a location that is at least 1 cm away from bowel. In addition to the use of oral WR-2721 for improving the outcomes for pancreatic cancer patients, a similar strate Gy may be for other abdominal or pelvic cancers that cannot be treated definitively with radiation due to GI toxicity, such as hepatobiliary tumors, retroperitoneal sarcomas, or metastatic disease within the abdomen.

The entire intestinal tract is enriched with intestinal alkaline phosphatases, which exhibit the highest levels of expression in the duodenum and jejunum. Thus, it was reasoned that a dose of S-2-(3-aminopropylamino)ethyl dihydrogen phosphorothioate (hereinafter WR-2721) having the formula:

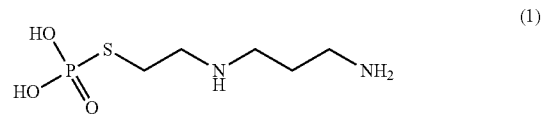 [SMILES: NCCCNCCSP(=O)(O)O]

(1)

given orally at a predetermined time before radiation could be rapidly activated by the endogenous digestive enzymes in the duodenum and jejunum to its active 2-[(3-Aminopropyl)amino]ethanethiol dihydrochloride (hereinafter WR-1065) (or its free monobase or dibase conjugate, devoid of the respective HCl and any other pharmaceutically acceptable salt formation once passage into or through the duodenum) metabolite having the formula:

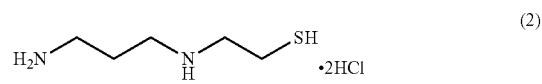

(2)

Due to the increased expression of non-tissue specific alkaline phosphatase in the intestine, enterally-activated form of WR-2721 would accumulate in high concentrations in the intestines and provide selective localized radioprotection with fewer systemic side effects. This can be useful during radiation for pancreatic cancer, since the duodenum and jejunum are dose-limiting organs preventing ablative treatments. The disclosure shows that oral WR-2721 is an effective radioprotector against otherwise lethal doses of radiation directed to the upper abdomen. Furthermore, demonstrated herein is the fact that the drug is well-tolerated and accretes its active metabolite, WR-1065, in significantly higher levels in the GI tract compared to the serum, liver or spontaneous pancreatic tumors. Such a localization effect is not accessible by IV administration of WR-2721.

An "effective amount" of a subject compound, with respect to the present methods of treatment, refers to an amount of the cytoprotective pro-drug in a preparation which, when applied as part of a desired dosage regimen (dose, timing, frequency), prevents from bringing about, e.g., a change in rate of survival of a cell according to clinically acceptable standards for the disorder to be treated. Also, as used herein, the term "accrete" and its grammatical derivatives e.g., "accretive" or "accretivly", refer in an embodiment to the gradual increase in concentration of the active metabolite in the target tissue and/or organ that is to be radiation-protected.

Accordingly and in an embodiment, provided herein is a method for treating a cancer patient in need thereof, with a combination therapy comprising: administering to the patient a therapeutically effective, orally dosed cytoprotective pro-drug at a predetermined time prior to exposure to radiation, the patient having at least one of a primary and a metastatic cancer in at least one of a tissue and an organ adjacent to at least one of other tissues and other organs sensitive to radiation, wherein the pro-drug is configured to selectively accrete in at least one of the other tissue and other organ sensitive to the therapeutically effective radiation dose; and exposing the at least one tissue and one organ to a therapeutically effective radiation dose.

In an embodiment the cytoprotective pro-drug is WR-2721. As used herein, the term "pro-drug" refers to a pharmacologically inactive form of a compound that undergoes biotransformation prior to exhibiting its pharmacological effect(s). A pro-drug is one that is metabolized in vivo by a subject after administration into a pharmacologically active form of the compound in order to produce the desired pharmacological effect. After administration to the subject, the pharmacologically inactive form of the compound is converted in vivo under the influence of biological fluids and/or enzymes into a pharmacologically active form of the compound. Although metabolism occurs for many compounds primarily in the liver and/or kidney, almost all other tissues and organs, especially the lung, are able to carry out varying degrees of metabolism. Pro-drug forms of compounds can be utilized, for example, to improve bioavailability, mask unpleasant characteristics such as bitter taste, alter solubility for intravenous use, or to provide site-specific delivery of the compound. Reference to a compound herein includes pro-drug forms of a compound and the drug conjugate (active form).

The oral dosage forms of WR-2721 can be also be a part of a composition comprising salt of a chelating agent selected from the group consisting of EDTA, EGTA, citrate and therapeutically acceptable salts thereof. For oral administration, the formulations may be prepared as liquids, solutions, suspensions, capsules, tablets, coated tablets, and other standard procedures known in the art. For rectal application, the formulations may be prepared as liquid enemas, microenemas, suppositories, rectal tablets, and other standard procedures known in the art. A preferred formulation can be made with the pharmacologically required dose of WR-2721 being between about 150 mg/kg and about 1000 mg/kg, for example, between about 250 mg/kg and about 750 mg/kg or about 500 mg/kg, and, for rectal applications, sufficient suppository base to formulate an acceptable composition. The methods and choice of excipients and suppository bases are well known to those skilled in the art, and the compositions of said formulations are not limited to gelatin capsules, compressed tablets or solid suppositories by this invention.

In an embodiment, the at least one of the primary cancer and the metastatic cancer is at least one of a pancreatic cancer and a prostate cancer. As used herein, "primary cancer" refers to the original site (organ and/or tissue) where a cancer originates. Exemplary primary cancers may be located in the head, neck, nasal cavity, paranasal sinuses, nasopharynx, oral cavity, oropharynx, larynx, hypopharynx, salivary glands, paragangliomas, pancreas, stomach, skin, esophagus, liver and biliary tree, bone, intestine, colon, rectum, ovaries, prostate, lung, breast, lymphatic system, blood, bone marrow central nervous system, or brain. Conversely, the term "metastatic cancer" refers to a cancer in which cells of the cancer have metastasized, e.g., the cancer is characterized by metastasis of a cancer cells. The metastasis can be regional metastasis or distant metastasis. Also, the term "metastatic" is intended to mean that metastasis is observed when assayed by a method used to evaluate the metastatic ability of cells. For example, in a case where cells are transplanted into laboratory animals, this term refers to a state that the cells form distant metastasis. Likewise, the term "metastatic cancer cells" refers to cancer cells having a metastatic potential.

In an embodiment, the tissues sensitive to radiation is the duodenum and/or jejunum. For example, given as conventionally fractionated therapy, typical limits for maximum radiation dose to the duodenum are thought to be about 50 Gray (Gy) to one-third of the organ or 40 Gy to the entire organ, with recent guidelines recommending that only 195 $cm^3$ of small bowel receive >45 Gy. Conversely, as disclosed herein, biologically effective doses in (large) excess of 55 Gy may be necessary to achieve a high probability of tumor control. Accordingly and in an embodiment, the step of exposing the at least one tissue and one organ to a therapeutically effective radiation dose comprises using stereotactic body radiation therapy (SBRT), administrating to the patient a total radiation dose of between about 5 Gy, and about 16 Gy per fraction for a total of between one and five fractions (25-80 Gy), which would be a total BED10 of 37.5 Gy-208 Gy in three to five fractions or an D2EQ of 31.25 Gy to 173.3 Gy on three to five fractions.

In stereotactic body radiation therapy (SBRT), a single or limited number of focused, high dose radiation fractions are configured to be delivered to the tumor, which enables the delivery of ablative doses to the tumor and immediately adjacent tissues. In an embodiment, SBRT can be an alternative to resection when a critical structure, which precludes its surgical resection, is presented. Moreover, in another embodiment, the methods disclosed further comprise treatment planning using, for example, respiratory-correlated cone-beam computed tomography (4D-CT), with abdominal compression to limit the respiratory-associated movement of tumor during the step of delivering the fractionated radiation. In certain embodiments, fiducial markers are used during the course of treatment to actively track tumor movement.

The radiation can commence between 15 minutes and about 30 minutes following the administration of the oral dosage of about 250 mg/kg to about 1000 mg/kg of an oral composition comprising WR-2721. For example, 25 minutes might be chosen, wherein the radiation is fractionated (thus taking advantage of the deficient DNA repair mechanisms of cancer cells compared with healthy cell). The number of fractions can be, for example, between 1 and 5, for example 5 radiation fractions, each given between about 15 minutes and about 30 minutes post administration of oral (and/or rectal) composition comprising the WR-2721. The dosage delivered per fraction (assuming five fractions) can be between about 11 Gy and about 15 Gy, for example, between about 12 Gy and about 15 Gy, or between about 12.5 Gy and about 13 Gy per fraction. Total radiation dose can be, for example, between 55 Gy and about 130 Gy and will depend on at least one of, for example, the tumor location, the tumor classification, and the type of cancer associated with the tumor.

Accordingly and in another embodiment, provided herein is a method of protecting at least one of a first tissue and a first organ, the first tissue and/or organ being sensitive to radiation in a patient in need of a high dose radiation, from the high dose radiation to at least one of an adjacent second organ and an adjacent second tissue, comprising a step of administering to the patient an oral composition comprising a pharmaceutically effective concentration of a cytoprotective agent having a metabolite adapted to selectively accrete in at least the first tissue and the first organ, wherein the oral composition is administered at a predetermined time prior to radiation.

In certain embodiments, the oral dosages disclosed herein, comprise pharmaceutically acceptable compositions which comprise a therapeutically-effective amount of one or more of the compounds described above, namely WR-2721, it analogs and pharmaceutically acceptable salts thereof, formulated together with one or more pharmaceutically acceptable carriers (additives) and/or diluents. The pharmaceutical compositions provided herein may be specially formulated for administration in solid or liquid form, including those adapted for at least one of the following: (a) oral administration, for example, drenches (aqueous or non-aqueous solutions or suspensions), tablets, e.g., those targeted for buccal, sublingual, and systemic absorption, capsules, boluses, powders, granules, pastes for application to the tongue; (b) intravaginally or intrarectally, for example, as a pessary, cream or foam; and (c) sublingually.

Examples of suitable aqueous and nonaqueous carriers which may be employed in the pharmaceutical compositions provided herein, can include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, dispersing agents, lubricants, and/or antioxidants. Prevention of the action of microorganisms upon the compounds of the present invention may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. In addition, the oral compositions provided herein may also comprise an acceptable buffering agent mixture (e.g., tris buffer, phosphate buffer, and the like); a sweetening agent; and/or at least one flavor agent.

Actual dosage levels of the active ingredients in the pharmaceutical compositions provided herein, can be varied so as to obtain an amount of the active ingredient (e.g., WR-2721) that is effective in achieving the desired therapeutic response for a particular patient, composition, and mode of administration, without being toxic to the patient. The selected dosage level will depend upon a variety of factors including the activity of the particular compound provided herein, can employed, or the ester, salt or amide thereof, the route of administration, the time of administration, the rate of excretion or metabolism of the particular compound being employed, the rate and extent of absorption, the duration of the treatment, other drugs compounds (e.g., oxaliplatin, irinotecan, fluorouracil, leucovorin, gemcitabine in the case of metastatic pancreatic cancer), and/or materials used in combination with the particular compound employed, the age, sex, weight, condition, general health and prior medical history of the patient being treated, and like factors and their combination.

The terms "treat," and "prevent" as well as words stemming therefrom, as used herein, do not necessarily imply 100% or complete treatment or prevention (for example, preventing damage to adjacent tissue). Rather, there are varying degrees of treatment or prevention of which one of ordinary skill in the art recognizes as having a potential benefit or therapeutic effect. In this respect, the methods disclosed and claimed herein, can provide any amount of any level of diagnosis, staging, screening, or other patient management, including treatment or prevention of cancer in a mammal. Furthermore, the treatment or prevention provided by the methods disclosed and claimed herein, can include treatment or prevention of one or more conditions or symptoms of the disease, e.g., cancer, being treated or prevented. Also, for purposes herein, "prevention" can encompass delaying the onset of the disease, or a symptom or condition thereof.

The terms "first," "second," and the like, herein do not denote any order, quantity, or importance, but rather are used to denote one element from another. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the tumor(s) includes one or more tumor). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

EXAMPLES

Materials and Methods

Mice

C57BL/6JLaw and C3Hf/KamLaw mice were purchased from the Department of Experimental Radiation Oncology's specific pathogen free animal facility at the MD Anderson Cancer Center. $Kras^{LSL/+}$; $Trp53^{FL/+}$; $Ptfla^{Cre/+}$ mice were backcrossed to a pure C57BL/6 background over ten generations genotyped as described previously[28]. All mice were acquired and maintained in accordance with the Association for Assessment and Accreditation of Laboratory Animal Care and the Institutional Animal Care and Use Committee guidelines and experiments were performed under an institutionally-approved protocol for the Taniguchi Lab. Female C3Hf/KamLaw mice were used for the microcolony assay[13] and were 12-14 weeks old at the start of treatment. Tumor-bearing KPC mice were used in the LC/MS-MS tissue analysis of WR-1065 concentrations. The remaining studies use male C57BL/6JLaw mice at 8 weeks of age at the start of all studies.

WR-2721

WR-2721 Trihydrate (Toronto Research Chemicals Inc; North York, Ontario, Canada) was diluted in PBS (with 0.2 conversion factor to adjust for trihydrate) and was administered by IP injection at 25 or 250 or 500 mg/kg or by oral gavage at doses from 5 from 150 to 1000 mg/kg in a volume of 0.1 ml.

Irradiation

For survival studies, SBRT was given for 5 consecutive days 25 min after administration of vehicle or WR-2721 using the XRAD 225Cx small animal irradiator (Precision X-Ray; North Branford, Conn.) fitted with a conformal collimator to produce a circular 10 mm diameter radiation field. Mice were anesthetized with isoflurane gas for CT imaging and irradiation. Each mouse was imaged using the XRAD 225Cx cone beam CT prior to irradiation in order to align the radiation field so that the cranial edge of the field was located 5 mm below the diaphragm at the isocenter of the mouse. This field exposed the pancreas, duodenum, jejunum and liver to radiation. Radiation was administered anterior-posterior-posterio-anterior (AP-PA).

For the microcolony assay, a single dose of 12 Gy whole body irradiation (WBI) was administered 15 min or 30 min after WR-2721 treatment using a Pantak 300 x-ray unit (Pantak; East Haven, Conn.), with 300 kVp X-rays at a dose rate of 1.84 Gy/min. Un-anesthetized mice were loosely restrained in a well ventilated 15×15×2 cm Lucite box during WBI.

Methylene Blue Gut Assay

In order to determine the rate at which oral solutions such as WR-2721 traverse the digestive tract of 8-week old C57BL/6 mice following oral gavage, a 1% (w/v) solution of methylene blue in PBS was gavaged in a total volume of 0.1 ml. Mice were then euthanized at 5, 10, 15, 25 and 30 min after the dye administration and the progress of the methylene blue stain through the intestines was examined. Mice were anesthetized with isoflurane 8 min prior to euthanasia following the same procedure used prior to irradiation (8 min at 3% isoflurane and oxygen flow rate of 2 L/min) to account for any potential changes it might have on GI transit time. Methylene blue dye progress was examined in situ for comparison with the location of our standard radiation field and then the intestine was excised so that distance traveled could be determined.

Survival Studies

Mice were treated with WR-2721 or vehicle by intraperitoneal (IP) injection or oral gavage followed by SBRT and monitored on a daily basis. Once mice became moribund (exhibited ruffled fur, hunched posture, persistent diarrhea and greater than 20% weight loss) they were euthanized. Time to euthanasia and percent survival were assessed.

Microcolony Assay

Viable jejunal crypts were quantified following a single dose of 12 Gy WBI+/− a single oral dose of WR-2721 given at 15 min or 30 min prior to radiation using the microcolony assay. Mice were euthanized 3 days and 14 hours after receiving WBI, and segments of jejunum and duodenum were resected and fixed in 10% neutral buffered formalin. Tissue was then embedded in paraffin, and four transverse slices of jejunum and duodenum were stained with hematoxylin and eosin per mouse. The number of regenerating crypts per transverse section was scored microscopically and averaged over the 4 sections per animal for each tissue type. All slides were scored by a single observer blinded to treatment group.

LC/MS-MS Analysis of WR-1065 Tissue Concentrations

Mice were treated with either 500 mg/kg of WR-2721 by oral gavage, or 250 mg/kg by IP injection. After 17 min had elapsed, the mice were anesthetized with isoflurane gas (3% isoflurane, oxygen flow rate of 2 L/min). After 8 min of anesthesia, whole blood and tissues were collected. The total amount of time between treatment and tissue collection was 25 min.

While under isoflurane anesthesia, the whole blood sample was collected via cardiac puncture and was immediately transferred to a BD Microtainer® blood collection tube containing $K_2$-EDTA (Becton Dickinson; Franklin Lakes, N.J.). The $K_2$-EDTA whole blood was then processed to plasma by centrifugation at 3,000 g for 4 min. After processing, a volume of the plasma supernatant (typically 200 µL) was removed and immediately transferred to a fresh 1.4 mL Matrix polypropylene (PP) tube (Thermo Fisher Scientific; Waltham, Mass.) containing a 50 µL aliquot of 10% trichloroacetic acid (TCA). After vortexing, the TCA-treated plasma samples were stored on ice for transport from the vivarium to the laboratory for further processing. The TCA-treated plasma samples were then centrifuged at 17,000 g for 5 min, and the supernatant was transferred to a fresh 1.4 mL Matrix tube, and the samples were either extracted and analyzed immediately or capped for −80° C. storage until analysis.

After blood collection, the mouse was euthanized, the duodenum, jejunum, liver, and tumor tissue samples were collected, and each tissue sample was placed into individually labeled PP tubes and weighed. After weighing, an aliquot of 2% TCA was added to each tube (the tissue density at 200 mg tissue per mL of solution or below for all samples), and the tissues were homogenized using a Polytron PT 1200 E hand-held homogenizer. After homogenization, the TCA-treated tissue samples were stored on ice for transport from the vivarium to the laboratory for further processing. The TCA-treated tissue samples were then centrifuged at 4,500 g for 5 min, and the supernatant was transferred to a fresh 2 mL Simport tube (Simport; Montreal, Canada), and the samples were either extracted and analyzed immediately or capped for −80° C. storage until analysis.

Preparation of the 2% TCA (w/v) Treated C57BL/6 Mouse $K_2$-EDTA Plasma Matrix

A 2% TCA (w/v) treated plasma matrix solution was prepared by combining 0.400 mg TCA with 20 mL of C57BL/6 mouse K2-EDTA plasma (BioreclamationIVT; New York, N.Y.) in a 50 mL Falcon PP conical tube (Thermo Fisher Scientific). The mixture was vortexed for 2 min and centrifuged at 4,500 g for 5 min to settle all of the precipitated protein. The 2% TCA-treated plasma matrix supernatant was transferred into two 15 mL PP tubes for long-term storage. The 2% TCA plasma matrix was maintained ice-cold while in use, and stored at −80° C. when not in use.

Preparation of the 2% TCA (w/v) Treated C57BL/6 Mouse Duodenal Tissue Matrix

A 2% TCA treated duodenal tissue matrix solution was prepared by combining individually weighed duodenal tissue samples (BioreclamationIVT) with 1.6 mL of an aqueous 2% TCA solution in hard homogenization tubes (Bertin Instruments; Bretonneux, France), and homogenized using the pre-programmed hard tissue sample setting for two cycles using the Precellys® Evolution tissue homogenizer (Bertin Instruments). Afterwards, the homogenized tissue matrix was centrifuged at 17,000 g for 5 min to settle the tissue debris. The 2% TCA-treated duodenal tissue matrix supernatant in each tube was transferred into a 15 mL PP tube for long-term matrix storage. The 2% TCA duodenal matrix was maintained ice-cold while in use, and stored at −80° C. when not in use.

Preparation of WR-2721 and WR-1065 Stock and Intermediate Solutions

WR-2721 reference standard (US Pharmacopeia USP; Rockville, Md.) and WR-1065 (Sigma-Aldrich; St. Louis, Mo.) stocks were prepared in aqueous 10 mM ammonium acetate (pH 9.2) or aqueous 2% TCA solutions, respectively. Intermediate-concentration solutions were prepared at 100 µg/mL for each compound using consistent solvents mixed 1:1 with acetonitrile.

Preparation of WR-1065 Calibration Standards

Two separate sets of WR-1065 calibration standards (Calibrators) were prepared by serial dilution using either 2% TCA-treated plasma matrix or 2% TCA-treated duodenal matrix as the diluent. After the preparation of each Calibrator in each set, the standard was vortexed for a minimum of 30 s to ensure proper mixing prior to performing the subsequent dilution. The Calibrators were prepared at 1.00, 2.00, 10.0, 100, 250, 500, 900, and 1,000 ng/mL in each matrix. The Calibrators were prepared and stored individually in labeled 2 mL Simport tubes, were maintained ice-cold while in use, and stored at −80° C. when not in use.

Extraction Method for the 2% TCA-Treated Plasma and Tissue Samples

All calibrators, 2% TCA blank plasma matrix and study samples were thawed and stored on ice for the duration of the extraction procedure. A 2 µL aliquot of an ice-cold aqueous 10% TCA (w/v) solution was added to each 1.4 mL PP Matrix sample tube. A 10 µL aliquot of each Calibrator, blank sample matrix, and study sample was added to the appropriate tube. Then, a 90 µL aliquot of ice-cold acetonitrile was added to each tube, and the samples were capped and vortexed for 2 min. Finally, the samples were centrifuged at 17,000 g for 5 min, and then the supernatant was transferred to PP injection vials for sample analysis. A typical injection volume for analysis was 10 µL.

The extraction process for the 2% TCA-treated tissue samples was similar to the plasma extraction procedure described above, with the following exception—the tissue samples do not receive a 2 µL aliquot of an ice-cold aqueous 10% TCA solution. After performing the protein precipitation and centrifugation step as described above, the tissue sample supernatant was transferred to PP injection vials for sample analysis. A typical injection volume for analysis was 10 µL.

LC/MS-MS Method

LC/MS-MS analysis was performed using an Ultimate 3000 RSLC Ultra-High Performance Liquid Chromatography (UHPLC) system coupled to a TSQ Quantiva tandem-mass spectrometer (Thermo Fisher Scientific). A zwitterionic ZIC-pHILIC (150×2.1 mm, 5 µm particle size) analytical column (MilliporeSigma; Billerica, Mass.) was used to achieve baseline separation of WR-2721 and WR-1065 using mobile phase A (MPA) and mobile phase B (MPB) compositions of 95/5 acetonitrile/200 mM ammonium formate with 2% formic acid, and 85/10/5 water/acetonitrile/200 mM ammonium formate with 2% formic acid, respectively. The chromatographic method included a column temperature of 40° C., autosampler tray chilled to 4° C., a mobile phase flow rate of 300 µL/min, and a gradient elution program specified as follows: 0-5 min, 50% MPB; 5-5.5 min, 50-80% MPB; 5.5-11 min, 80% MPB; 11-11.5 min, 80-50% MPB; 11.5-15 min, 50% MPB. The overall cycle time of the chromatographic gradient program was 15.5 minutes per sample. The blank plasma samples after the highest Calibrator (1,000 ng/mL) was free from carryover when a solution of 1:1 acetonitrile:water with 0.1% formic acid was used as the needlewash.

The TSQ Quantiva was operated in positive ion mode and had the following source parameters: source: H-ESI; source voltage:+3,200 V; sheath gas: 50; auxiliary gas: 20; sweep gas: 1; ion transfer tube temperature: 370° C.; vaporizer tube temperature: 250° C. The following SRM transitions for WR-1065 were monitored: i) m/z: 135.1→118 (quantifier), CE: 10.3 V; ii) m/z: 135.1→58 (confirming), CE: 16 V; and iii) m/z: 135.1→61 (confirming), CE: 22.5 V. The MS-MS system was operated in unit/unit resolution, with an RF Lens voltage of 59 V, and the dwell time of 200 ms for each SRM transition.

Statistical Analyses

Log-Rank analysis was used for survival studies and median survival was determined with 95% confidence interval (CI). Two tailed t-tests with unequal variance were used to compare PO vs. IP plasma and tissue concentrations of WR-1065. Values less than 0.05 were considered significant.

Dose Conversion

Body surface area (BSA) was used to translate the results obtained on mice to human equivalent dose (HED), in accordance with the FDA recommendations, using the formula:

$$HED = \text{Animal Dose (mg/kg)} \times [(\text{Animal } K_m)/(\text{Human } K_m)]$$

wherein: HED is the human equivalent dose in mg/kg
Animal $K_m$=3 (mice)
Human $K_m$=37

(see e.g. (Center for Drug Evaluation and Research, Center for Biologics Evaluation and Research. (2002) *Estimating the safe starting dose in clinical trials for therapeutics in adult healthy volunteers*, U.S. Food and Drug Administration, Rockville, Md., USA).

EXAMPLE I

Oral WR-2721 Promotes Intestinal Crypt Survival after Irradiation

Figure 1:
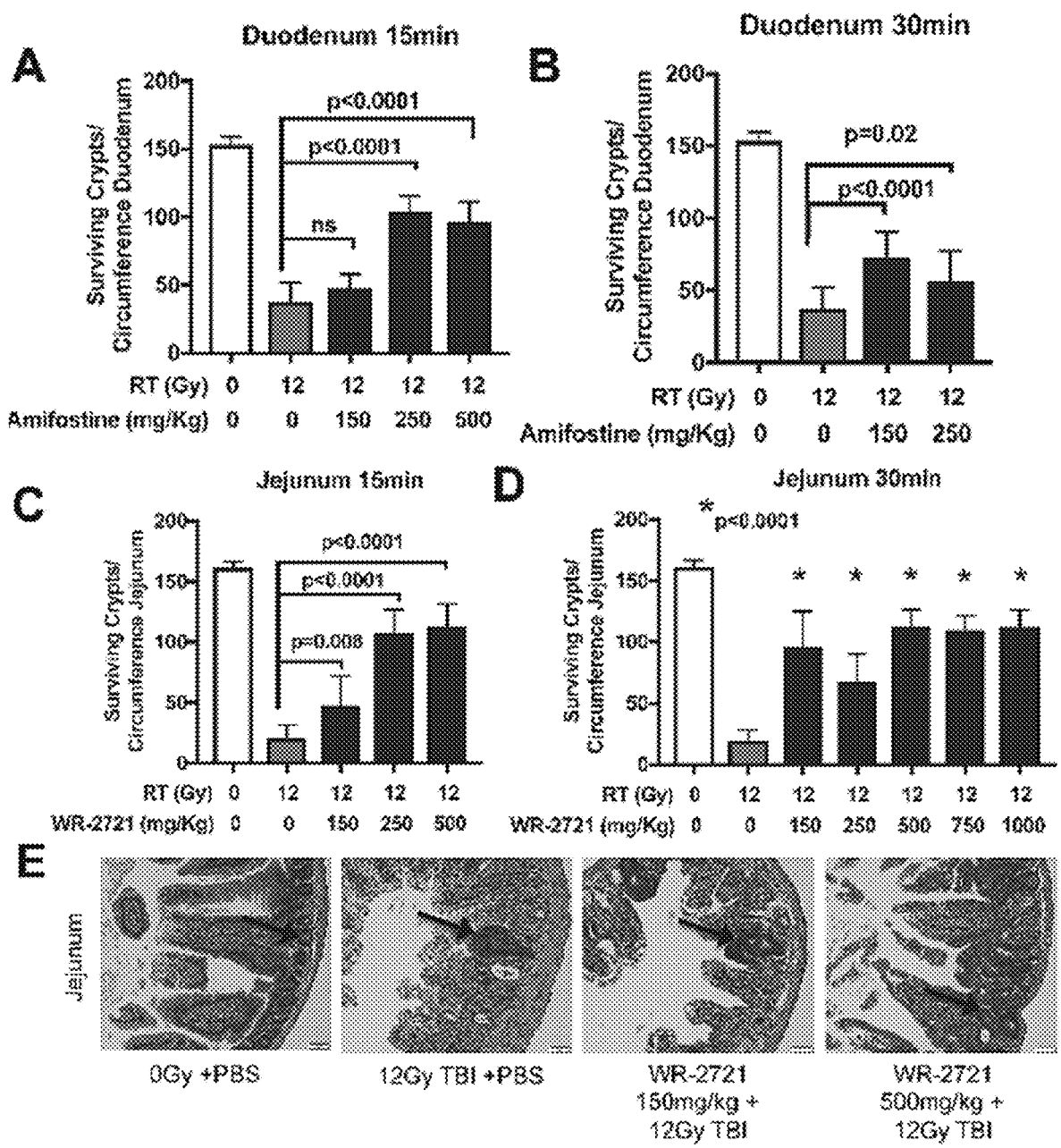
FIG. 1, shows oral WR-2721 able to Improve Intestinal Crypt Survival after Lethal Radiation. Withers-Elkind microcolony assay was performed and surviving crypts per duodenal and jejunal cross-section following treatment was quantitated for the following groups: Duodenum: (A) WR-2721 given PO 15 minutes prior (n=6-20/group) or (B) 30 minutes n=6-20/group) prior to 12 Gy WBI. Jejunum: (C) WR-2721 given PO 15 minutes prior (n=6-20/group) or (D) 30 minutes n=6-42/group) prior to 12 Gy WBI. (E) Representative H&E used in (C) and (D) with arrows highlighting surviving crypts.

Systemic dosing of WR-2721 by intraperitoneal (IP) injection has already been shown to be effective at radio-protecting the gut of C3Hf/KamLaw mice receiving whole body irradiation, however, it was sought to determine if oral (PO) administration of WR-2721 would be similarly efficacious. A range of doses of oral WR-2721 from 0 to 1000 mg/kg were tested, followed by a morbid dose of whole body irradiation (WBI) either 15 or 30 minutes later. All mice were then subjected to a microcolony assay. Indeed, compared to vehicle controls, oral WR-2721 improved crypt survival in the duodenum when administered at either 15 or 30 min prior to WBI (FIGS. 1A and 1B). Similarly, oral WR-2721 also promoted crypt survival in the jejunum at both 15 min (FIG. 1C) and 30 min (FIG. 1D) after drug treatment. Oral WR-2721 protected the duodenum and jejunum at all doses and timepoints compared to PBS controls except the lowest dose in the duodenum at 15 min. A more extended dose response was carried out in the jejunum for WR-2721 given 30 min prior to 12 Gy of WBI, and it was concluded that radiation protection was maximized at 500 mg/kg (HED=41 mg/kg), with no further benefit conferred by doubling the dose to 1000 mg/kg (FIG. 1D, HED=81 mg/kg). Representative H&E stained jejunal sections from the microcolony assays are shown in FIG. 1E.

EXAMPLE II

Orally Administered WR-2721 is Better Tolerated than Intraperitoneal WR-2721

Figure 2A:
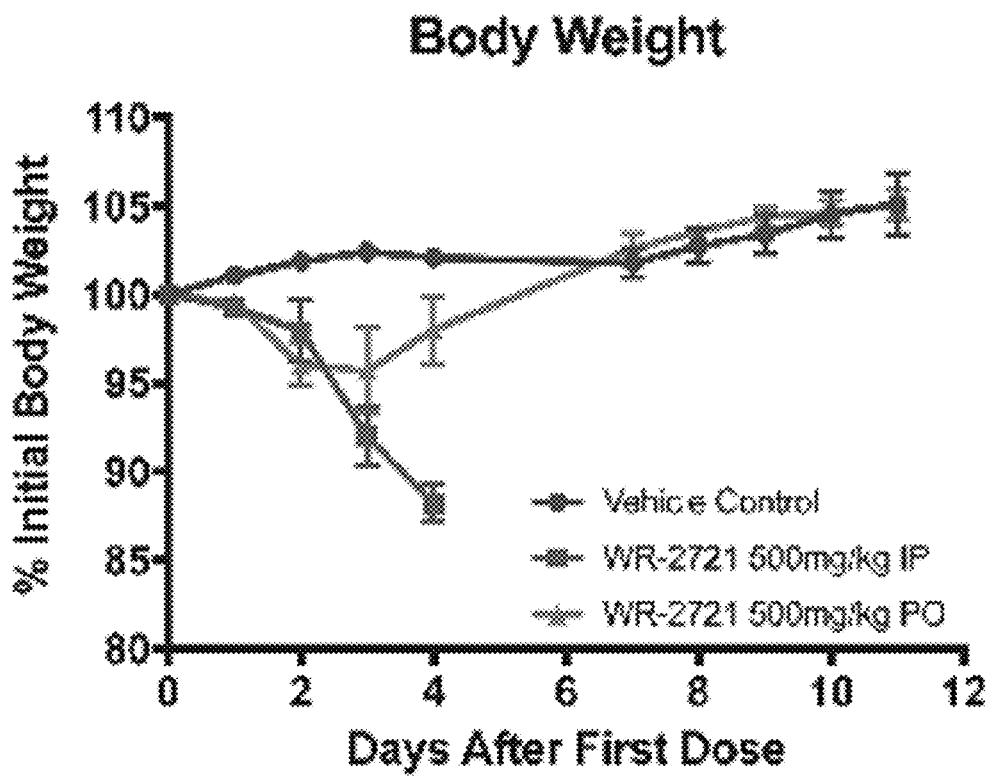
FIG. 2A, shows oral Administration of WR-2721 is Better Tolerated than Systemic Injections by Body weight and in 2B by food intake, both measured daily following administration of WR-2721 for 5 consecutive days by either oral gavage (triangles, n=6), IP injection (red squares, n=5), or vehicle control (circles, n=5)
Figure 2B:
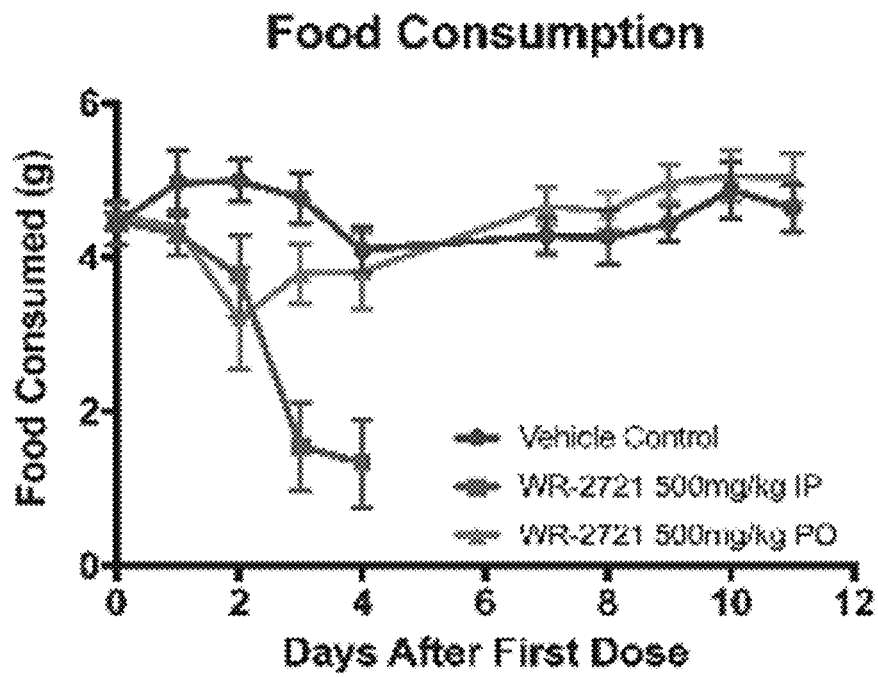

Severe nausea is a common and worrisome side effect of systemic WR-2721, and the concern that oral administration of the drug might exacerbate this side effect was examined. Although mice do not produce an emetic response to noxious stimuli, nausea can be manifested as a decrease in body weight and food intake. Thus, body weight and food consumption was closely monitored as a model of nausea in mice. Based on the results of the microcolony assay (FIG. 1), 500 mg/kg were used as the dose for toxicity testing. Mice were treated daily for 5 consecutive days with vehicle or WR-2721 administered IP or Per os (PO), and body weight and food consumption were monitored daily (FIGS. 2A and 2B, respectively). There was only one vehicle control group that was subjected to both gavage and intraperitoneal injections to more stringently control for the stress of drug administration from either IP or PO route. Despite this intensive intervention, the vehicle control animals maintained their initial bodyweight and food consumption throughout the study (FIGS. 2A and 2B). Mice receiving intraperitoneal WR-2721 at 500 mg/kg, however, exhibited a dramatic decrease in food consumption and body weight, requiring euthanasia by day 4 (FIGS. 2A and 2B). In contradistinction, mice receiving oral WR-2721 had a modest initial decrease in body weight and food consumption, but rapidly regained body weight with a complete recovery within 2 days of stopping treatment (FIGS. 2A and 2B). These data suggest that PO administration of WR-2721 is better tolerated than systemic administration and moreover, 500 mg/kg orally is an effective therapeutic dose for short-term radioprotection.

EXAMPLE III

WR-2721 Protects Against High-Dose Fractionated Radiation

In order to ablate pancreatic cancer with ionizing radiation, radioprotection of nearby duodenum and jejunum is required. It was reasoned that orally administered WR-2721 would be directly activated in the intestine as radiation is given to maximize efficacy without systemic absorption of the drug. The transit time of oral WR-2721 was modeled with a bolus of methylene blue and the progression of the dye front through the GI tract was assessed at 5-min intervals (FIG. 5). Methylene blue was found to have reached the duodenum within 10 min and was in the jejunum by 15-30 min (FIG. 5). Notably, within 30 min, the dye had not reached the cecum or large intestine. Thus, it was reasoned that oral gavage of WR-2721 25 min prior to irradiation could be used in future radioprotection.

Figure 3:
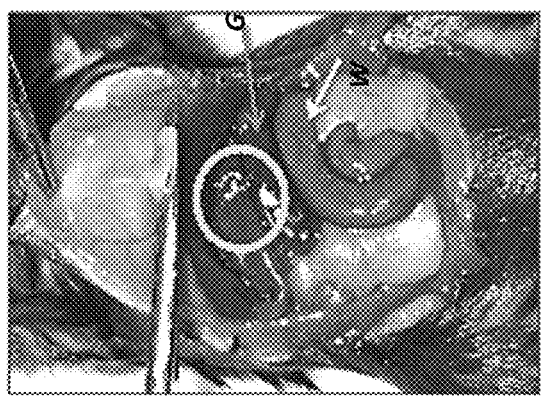
FIG. 3, shows oral WR-2721 improves survival after lethal fractionated radiation (A) Cone beam CT of a mouse taken just before irradiation with an overlay of where the 10 mm radiation field would be located. Tick marks within the reticle denote 5 mm intervals. (B) Mouse gavaged with methylene blue then dissected 25 minutes later. Blue dye is evident within the jejunum (arrow G), but not distal intestine (arrow W) at what would be the time of irradiation following a dose of WR-2721. (C) Mice were treated with 5 fractions of radiation given over 5 consecutive days using a 10 mm diameter circular radiation field (n=5/group). (D) Mice were treated with 500 mg/kg of WR-2721 by oral gavage 25 minutes prior to each fraction of 12.5 Gy for 5 consecutive days using a 10 mm diameter circular radiation field (n=5/group)
Figure 3:
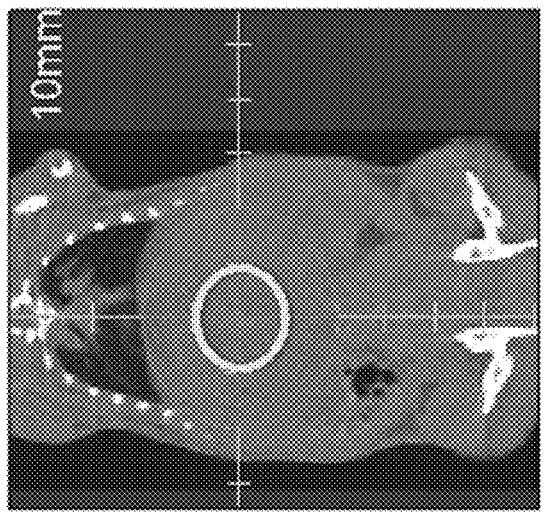
Figure 3:
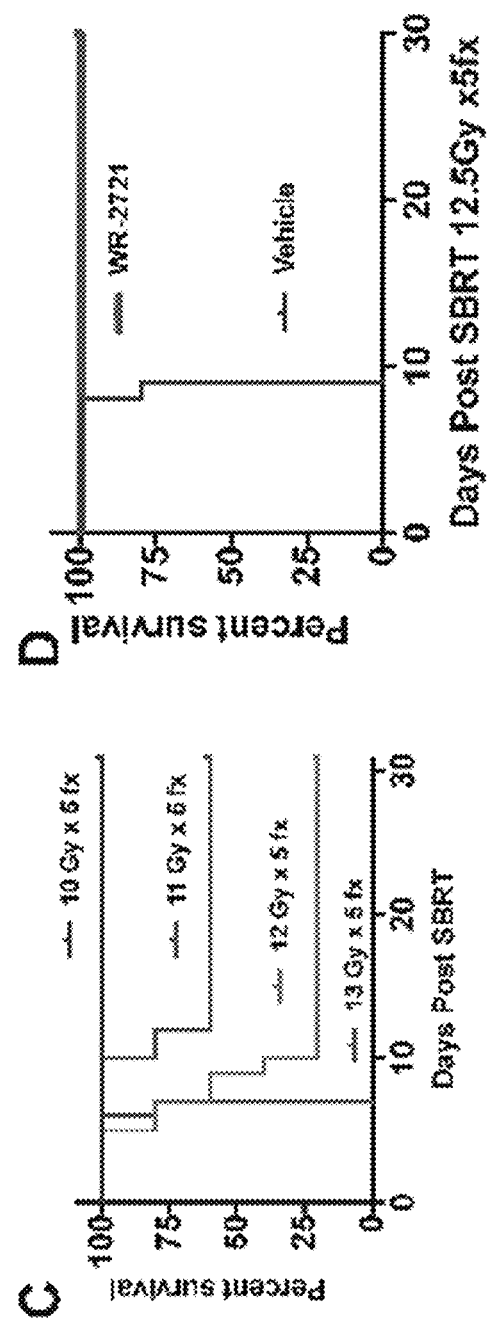

Stereotactic body radiotherapy (SBRT) can deliver higher and more conformal radiation doses to a smaller volume over a course of 1-5 treatments with the use of advanced image guidance. SBRT, however, is still constrained by the anatomy of the pancreas, where pancreatic tumors often abut or invade the nearby duodenum and jejunum. An SBRT treatment was designed, which used 10 mm. radiation fields that could be used to treat pancreatic cancer in mice (FIG. 3A). The radiological images were correlated with gross anatomy after methylene blue gavage indicated that even in this focused radiation field, a high dose was demonstrated to affect the entire pancreas, duodenum, and jejunum, along with a portion of the gastric antrum and the left lobe of the liver, which are anterior to the pancreas (FIG. 3B)

A standard radiation dose escalation study was performed to determine the LD50/10 (dose required to produce 50% lethality in 10 days or less) for this model of focused radiation. Daily fractions ranged from 10 to 13 Gy per fraction, and were given daily over 5 consecutive days. It was found, that 13 Gy×5 (65 Gy, D2EQ=124.6 Gy) led to 100% death in 10 days after treatment, and 10 Gy×5 (50 Gy, D2EQ=83.3 Gy) exhibited 100% survival at 30 days post-treatment (FIG. 3C). All other doses showed an intermediate phenotype, with a 20% 30-day survival at 12 Gy×5 (60 Gy; D2EQ=110 Gy) and a 60% 30-day survival of the cohort that received 11 Gy×5 (55 Gy, D2EQ=96.3 Gy).

To reiterate:

$$D2 \text{ equivalent}(D2EQ) = D1(\alpha/\beta + d1)/(\alpha/\beta + d2) \quad \text{(Equ. 1)}$$

where D2=equivalent total dose, D1=initial total dose, d1=initial dose/fraction and d2=wanted dose/fraction It was hypothesized that the maximal benefit of radioprotection would likely occur between 12 and 13 Gy at 12.5 Gy×5 fractions (62.5 Gy; D2Eq=117.2 Gy). Thus, a new cohort of mice was treated with 5 daily fractions of 12.5 Gy to the upper abdomen in a similar field as shown in FIG. 3A, with radioprotection afforded by orally administered WR-2721 or vehicle control 25 minutes prior to each radiation treatment. Remarkably, 100% of mice that received oral WR-2721 lived beyond 30 days, while all vehicle controls died in fewer than 10 days FIG. 3D, log rank p=0.0035).

Further confirmation is illustrated in FIG. 6. KPC Mice were enrolled onto the study shortly after diagnosis and were treated to vehicle alone, SBRT with vehicle or SBRT with oral WR-2721. The SBRT field was 10 mm given AP/PA to the tumor and the dose was 12.5 Gy per day for 5 consecutive days for a total dose of 62.5 Gy (EQD2=117.2 Gy; $\alpha/\beta_{10}$=140.6). The tumors were identified by micro CT and ultrasound on a daily basis without fiducials. Amifostine of vehicle was given 25 minutes prior to irradiation for each fraction.

As shown in FIG. 6, The median survival of VEH was 15 days (N=11), SBRT+VEH was 15 days (N=7) while the SBRT+WR-2721 was 40 days (N=5). Kaplan-Meier analysis showed that the SBRT+WR-2721 significant improved survival versus SBRT+VEH (Log-rank P=0.03) or VEH alone (Log-rank=0.03)

EXAMPLE IV

Selective Enrichment of WR-1065 within Intestines from Oral WR-2721

Oral WR-2721 was hypothesized to act via localized conversion to WR-1065 by intestinal alkaline phosphatases in the duodenum and jejunum. This would concentrate the active metabolite WR-1065 only in the dose-limiting areas of the intestine during radiation, and possibly reduce off-target effects. To understand if this was indeed the physiologic mechanism of action, a mass spectrometry assay was used to measure the concentrations of WR-1065, the active metabolite of WR-2721, in both serum and tissues. First, the pharmacokinetics of WR-1065 appearance in the plasma and other tissues after oral gavage was assessed, with 500 mg/kg or IP injection with 250 mg/kg (HED=20 mg/kg) of WR-2721 in C57BL/6 mice (see schema in FIG. 4A). Serum and tissues were collected 25 min after gavage, which approximates the distribution of WR-1065 in tissues at the time of radiation (FIG. 3C, 3D). The IP injection of WR-2721 resulted in almost a 5-fold increase in plasma concentrations of the active metabolite WR-1065, compared to oral administration (119.1±17.3 vs 27.0±7.0, IP vs oral, p=0.001, FIG. 4B). Tissues were harvested and immediately processed for metabolite collection 25 min after oral gavage or IP administration of WR-2721. IP injections were found to cause a nearly homogeneous concentration of the active metabolite WR-1065 in liver (254.3±34.1 pmol WR-1065/mg tissue), duodenum (237.7±22.7 pmol WR-1065/mg tissue), and jejunum (203.7±2.9 pmol WR-1065/mg tissue, FIG. 4C). Conversely, oral WR-2721, showed a six- to twelve-fold enhancement of WR-1065 within duodenum (586.2±97.0 pmol WR-1065/mg tissue) and jejunum (1141±104.8 pmol WR-1065/mg tissue) compared to liver (89.0±22.4 pmol WR-1065/mg tissue), indicating the specificity of tissue protection by the accretion of the oral WR-2721 metabolite WR-1065 in the tissue.

Next, the specificity of WR-1065 enrichment in intestines was determined in a genetically engineered mouse model. $Kras^{LSL/+}$; $Trp53^{FL/+}$; $Ptfla^{Cre/+}$ (KPC) mice that develop spontaneous pancreatic cancer were bred, and then backcrossed to a C57BL/6 background over 10 generations to eliminate the confounding issue of genetic variance from inbred mice. These autochthonous tumors are thought to recapitulate the desmoplasia observed in human tumors that may make these tumors more aggressive. To be an effective an effective clinical radioprotectant, WR-1065 should not accumulate in tumors. Thus, plasma, liver, duodenum, jejunum and pancreatic tumors were collected 25 min after oral administration of 500 mg/kg (HED=41 mg/kg), or IP administration of 250 mg/kg WR-2721 (HED=20 mg/kg) to determine the concentrations of the WR-1065 (see schema in FIG. 4D). Similar to results from wild-type C57BL/6 mice, IP injections of WR-2721 in KPC mice caused a 30-fold enrichment of WR-1065 in the serum compared to oral WR-2721, which did not reach statistical significance (FIG. 4E, p=0.07). IP injections of WR-2721 resulted in similar concentrations of the radioprotective metabolite WR-1065 in all tissues measured (FIG. 4F), in other words, non-selective accretion. The concentration of WR-1065 was 420±69.8 pmol WR-1065/mg tissue in the liver, 236.2±8.6 pmol WR-1065/mg tissue in the duodenum, 275.5±5.0 pmol WR-1065/mg tissue in the jejunum and 248±30.2 pmol WR-1065/mg tissue in pancreatic tumors.

The oral administration of WR-2721 exhibited a highly selective accretion of WR-1065 in the intestines (FIG. 4F). The concentration of WR-1065 was 200.6±23.3 pmol WR-1065/mg tissue in the duodenum and 757.7±26.8 pmol WR-1065/mg tissue in the jejunum compared to only 59.9±26.8 pmol WR-1065/mg tissue in the liver and 24.5±1.9 pmol WR-1065/mg tissue in the tumor. Thus, oral WR-2721 resulted in a 10 to 40-fold enrichment of the drug in the intestines compared to tumor (FIG. 4G), while systemic administration by IP injection caused an equal distribution of radioprotective drug in both the normal tissues and tumor.

Accordingly, orally administered WR-2721 was demonstrated to be well tolerated, and effective to radioprotect the intestinal tract from ablative doses of fractionated radiation. The natural gradient of intestinal alkaline phosphatases within the duodenum and jejunum was exploited to rapidly metabolize WR-2721 to the radioprotective WR-1065 within in the gut, while limiting exposure to the rest of the body where protection is not needed and in the case of tumors, would be counterproductive. This is illustrated in genetically engineered mice that show that WR-1065 significantly accrete at higher concentrations in intestines, but not within pancreatic tumors.

Moreover, alternative routes for WR-2721 administration have been tested previously with largely negative results. For example, endorectal infusion of amifostine was found to improve toxicity profiles after pelvic radiation in Phase I studies, but failed to meet endpoints in a larger randomized study. These may be due, in part, to reliance on the ubiquitous and non-specific alkaline phosphatases present in most cells. Moreover, the rectal mucosa has a thick mucus lining and expresses low levels of intestinal alkaline phosphatase, which is required to activate WR-2721. Accordingly and in another embodiment WER-2721 can be conjugated to or co-administered with alkaline phosphatase in a vehicle configured to cause its metabolite WR-1065 to accrete at the rectal mucosa to actuate the metabolism of WR-2721 to WR-1065 at effective concentrations.

Accordingly and in an embodiment, provided herein is a method for treating a cancer patient with a combination therapy, comprising: administering to the patient a therapeutically effective, orally dosed cytoprotective pro-drug at a predetermined time prior to exposure to radiation, the patient having at least one of a primary and a metastatic cancer in at least one of a tissue and an organ adjacent to at least one of other tissues and other organs sensitive to radiation, wherein the cytoprotective pro-drug metabolite is configured to selectively accrete in at least one of the other tissue and other organ sensitive to the therapeutically effective radiation dose; and exposing the at least one tissue and one organ to a therapeutically effective radiation dose, wherein (i) the cytoprotective pro-drug is S-2-(3-aminopropylamino)ethyl dihydrogen phosphorothioate (interchangeable with WR-2721 and amifostine), (ii) the at least one of the primary cancer and the metastatic cancer is at least one of a pancreatic cancer, a prostate cancer, a hepatobiliary tumor, and retroperitoneal sarcoma, (iii) the other tissues sensitive to radiation is the duodenum and/or (iv) the jejunum, wherein (v) the cytoprotective pro-drug is in a thiol form, wherein (vi) the step of exposing the at least one tissue and one organ to a therapeutically effective radiation dose comprises using stereotactic body radiation therapy, administrating to the patient a total radiation dose of between about 37.5 Gray (Gy) and about 208 Gy, wherein (vii) the step of exposing comprises using stereotactic fractionated radiation, (viii) administered in between 1 and about 5 fractions, wherein (ix) the predetermined time prior to exposure to radiation is between about 15 minutes and about 30 minutes, wherein (x) the therapeutically effective oral dose comprises between about 250 mg/kg and about 1000 mg/kg, and wherein (xi) the radiation is administered in between 3 and 5 fractions of 5 Gy and 16 Gy per fraction, wherein (xii) the predetermined time prior to exposure to radiation is about 25 minutes.

In another embodiment, provided herein is a method of protecting at least one of a first tissue and a first organ, the first tissue and/or organ being sensitive to radiation in a patient in need of a high dose radiation, from the high dose radiation to at least one of an adjacent second organ and an adjacent second tissue, comprising a step of administering to the patient an oral composition comprising a pharmaceutically effective concentration of a cytoprotective agent having a metabolite adapted to selectively accrete in at least the first tissue and the first organ, wherein the oral composition is administered at a predetermined time prior to radiation, wherein (xiii) the first tissue and/or first organ is at least one of a gastrointestinal tract, duodenum, jejunum, small intestine, large intestine, rectum, esophagus, stomach, bladder, and urinary tract, wherein (xiv) the at least one of the second tissue and the second organ is a pancreas, a prostate, a liver, a gallbladder, and adrenal gland, a kidney, the retroperitneum, a lymph node, a uterus, a testicle, an ovary, wherein (xiv) the high-dose radiation is at least a total dose of 15 Gy, wherein (xv) the cytoprotective agent is S-2-(3-aminopropylamino)ethyl dihydrogen phosphorothioate (interchangeable with WR-2721 and amifostine), wherein (xvi) radiation further comprises a step of using fractionated stereotactic body radiation therapy, exposing the at least one of the second tissue and the second organ to between 1 and about 5 irradiation fractions, wherein (xvii) the step of exposing the at least one tissue and one organ to a therapeutically effective radiation dose comprises administrating to the patient a total radiation dose of between about 15 Gy and about 208 Gy, wherein (xviii) the second organ is the pancreas and the first tissue is at least one of the duodenum and the jejunum, wherein (xix) the oral composition is administered between about 15 min. and about 30 min. prior to exposure to radiation, wherein (xx) the radiation is administered in between 3 and 5 fractions of 1.8 Gy and 16 Gy per fraction, and wherein (xxi) the therapeutically effective oral dose of the cytoprotective agent is between about 20 mg/kg and about 81 mg/kg.

In yet another embodiment, provided herein is use of orally dosed cytoprotective pro-drug in the manufacture of a medicament for the treatment of a cancer patient having at least one of a primary and a metastatic cancer in at least one of a tissue and an organ adjacent to at least one of other tissues and other organs sensitive to radiation, wherein the medicament is configured to be orally administered at a predetermined time prior to exposing at least one of the other tissue and other organ, to radiation.

While in the foregoing specification the devices for modulating and/or monitoring TEP described herein, and their methods of use have been described in relation to certain preferred embodiments, and many details are set forth for purpose of illustration, it will be apparent to those skilled in the art that the disclosure of the devices for modulating and/or monitoring TEP described herein and their methods of use are susceptible to additional embodiments and that certain of the details described in this specification and as are more fully delineated in the following claims can be varied considerably without departing from the basic principles of this invention.

What is claimed:

1. A method for treating a pancreatic cancer patient with a combination therapy, comprising:
    a. administering to the patient a therapeutically effective, orally dosed cytoprotective pro-drug that is S-2-(3-amino propylamino)ethyl dihydrogen phosphorothioate at between 15 minutes and 30 minutes prior to exposure to a stereotactic fractionated radiation, the patient having at least one of: a primary, and a metastatic cancer in the pancreas adjacent to at least one of: a duodenum, and a jejunum, wherein a metabolite of the therapeutically effective, orally dosed S-2-(3-amino propylamino)ethyl dihydrogen phosphorothioate is configured to selectively accrete in at least one of: the duodenum, and the jejunum; and
    b. timely exposing the pancreas to the stereotactic fractionated radiation.

2. The method of claim 1, wherein the step of exposing comprises administrating to the patient a total radiation dose of between about 50 Gray (Gy) and about 208 Gy.

3. The method of claim 1, wherein radiation is administered in between 1 and about 5 fractions.

4. The method of claim 3, wherein the radiation is administered in between 3 and 5 fractions of 10 Gy and 17 Gy per fraction, so long as the total dose is above 50 Gy.

5. The method of claim 1, wherein the therapeutically effective orally dosed cytoprotective pro-drug that is S-2-(3-amino propylamino)ethyl dihydrogen phosphorothioate comprises between about 250 mg/kg and about 1000 mg/kg.

6. The method of claim 1, wherein the predetermined time prior to exposure to radiation is about 25 minutes.

7. A method of protecting at least one of: a duodenum, and a jejunum in a patient in need of a high dose radiation, from an exposure to the high dose radiation to a pancreas, comprising a step of administering to the patient an oral composition comprising a pharmaceutically effective concentration of an orally dosed pro-drug that is S-2-(3-amino propylamino)ethyl dihydrogen phosphorothioate having a metabolite adapted to selectively accrete in at least one of: the duodenum, and the jejunum, wherein the oral composition is administered at between about 15 min. and about 30 min. prior to a administration of a stereotactic fractionated radiation.

8. The method of claim 7, wherein the high-dose radiation has a total dose of a least 50 Gy.

9. The method of claim 7 wherein the stereotactic fractionated radiation further comprises using fractionated stereotactic body radiation therapy, exposing the pancreas to between 1 and about 5 irradiation fractions.

10. The method of claim 9, wherein the high dose radiation has a total radiation dose of between about 50 Gy and about 208 Gy.

11. The method of claim 9, wherein the radiation is administered in between 3 and 5 fractions of 10 Gy and 17 Gy per fraction, so long as the total dose is at least 50 Gy.

12. The method of claim 11, wherein the therapeutically effective oral dose of the orally dosed pro-drug that is S-2-(3-amino propylamino)ethyl dihydrogen phosphorothioate is between about 20 mg/kg and about 81 mg/kg.

* * * * *